United States Patent [19]

Weissman

[11] Patent Number: 4,963,095
[45] Date of Patent: Oct. 16, 1990

[54] DENTAL PACKING INSTRUMENTS

[76] Inventor: Bernard Weissman, 225 E. 48th St., New York, N.Y. 10017

[21] Appl. No.: 312,547

[22] Filed: Feb. 17, 1989

[51] Int. Cl.$^5$ .............................................. A61C 1/07
[52] U.S. Cl. ..................................... 433/118; 433/114
[58] Field of Search ............... 433/118, 120, 122, 123, 433/124, 164, 116, 114

[56] References Cited

U.S. PATENT DOCUMENTS

| | | | |
|---|---|---|---|
| 907,815 | 12/1908 | Kelley | 433/123 |
| 1,382,821 | 6/1921 | Coates | 433/120 X |
| 3,516,161 | 6/1970 | Ellman | 433/124 |
| 3,727,315 | 4/1973 | Spinello | 433/124 |
| 4,341,519 | 7/1982 | Kuhr et al. | 433/122 |
| 4,460,341 | 7/1984 | Nakanishi | 433/122 |

FOREIGN PATENT DOCUMENTS 488577  7/1938  United Kingdom ................ 433/122

*Primary Examiner*—Robert P. Swiatek
*Assistant Examiner*—Nicholas D. Lucchesi
*Attorney, Agent, or Firm*—Paul J. Sutton; Barry G. Magidoff; Anthony Amaral, Jr.

[57] ABSTRACT

There is provided an apparatus for pressing into place, in the sub-gingival area, packing to separate a tooth and the soft tissue, or sulcus, in preparation for carrying out dental procedures. In a first embodiment, a mechanically driven packing hammer is provided for pressing conventional cord packing into place. The packing hammer comprises a reciprocating drive, a hammer comprising an elongated shank operatively and directly, but removably, connected to the reciprocating drive, and a hammer head rigidly secured to the shank; the hammer head is secured to the shank end distal from the reciprocating drive. The end surface of the hammer head is concave and extends substantially transverse to the axis of the shank. An external guide, rotatably secured to the reciprocating drive at a first end, extends along the length of, and substantially coaxial with and surrounding, the hammer. The external guide means has an opening at the second end, distal from the reciprocating drive so as to permit reciprocal movement of the hammer end surface from a first position inward of the guide to a second position substantially coterminous with the second end of the guide.

5 Claims, 5 Drawing Sheets

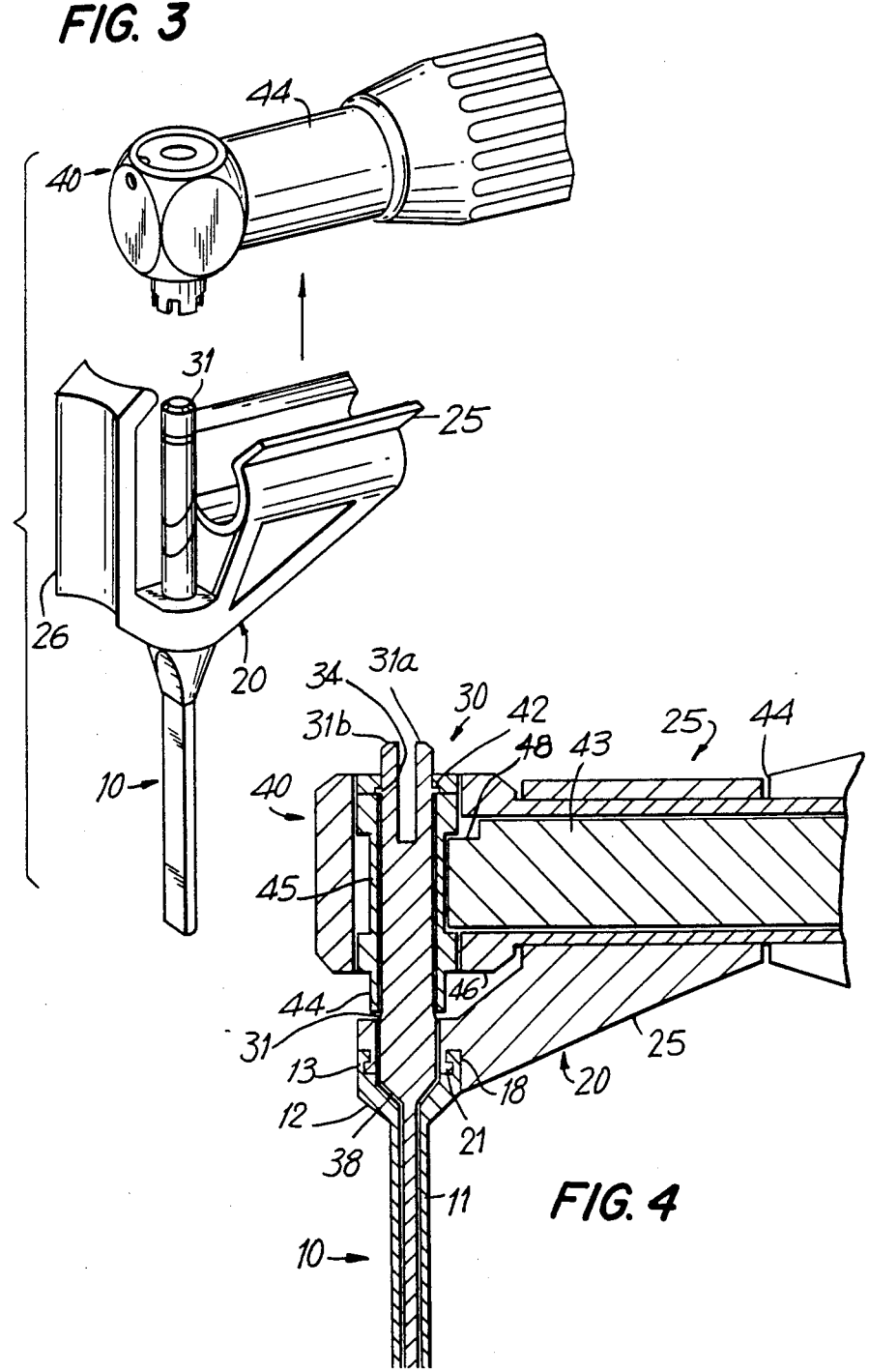

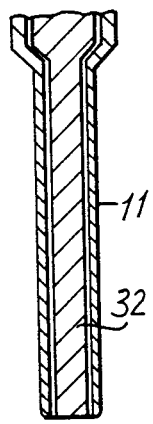
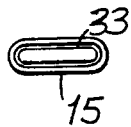
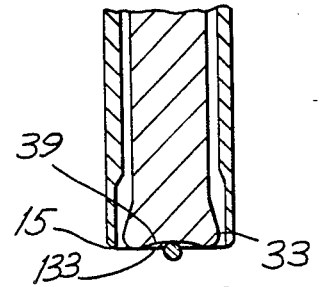
FIG. 5    FIG. 7    FIG. 6
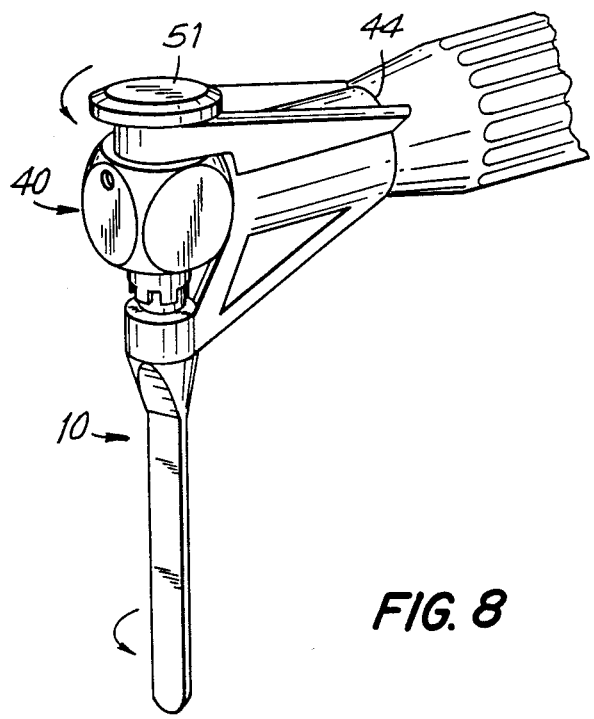
FIG. 8

DENTAL PACKING INSTRUMENTS

BACKGROUND OF THE INVENTION:

This invention relates to dental accessories, and more particularly to apparatus, and a method for utilizing the apparatus, for deflecting the gingival area about a tooth prior to, and in order to render more accurate, the forming of negative impressions of relevant teeth in a patient's mouth.

In the restoration or replacement (by a prosthesis), of teeth or portions of teeth, as by the production of crowns or dental bridges and the like, it is common procedure to form an elastic mold from which a model is made for the formation of the dental prosthesis, or a cap or crown. This mold, or dental model, is generally formed as a negative impression, as an imprint of a prepared tooth and the surrounding gum area. The mold is then used in the construction of a model or case on which replacement teeth are made for the patient.

The prosthesis is formed from the negative impression in the mold. It is clear, therefore, that this mold impression must be accurate, in order to form the desirably accurate prosthesis. A sufficiently accurate mold for forming the prosthesis, must include not only impressions of the normally visible portions of the tooth to be molded, but also that portion of the tooth which normally extends just below the gum line or gingiva, i.e., the so-called "margin", of the tooth. Conventionally, this is obtained by packing a woven cord, or thread, around the margin of the tooth, so as to hold aside the soft tissue and to also dry out this socket adjacent the tooth, i.e., the sulcus. This is normally a laborious task where the dentist manually pushes in a strand of cord into the sulcus utilizing a dental probe moving around the circumference of the tooth. An alternative, where possible is to cut away the gum line from the tooth in order to gain access to the terminal portion of the prepared tooth.

SUMMARY OF THE INVENTION:

It is an object of the present invention to provide improved apparatus to pack, more quickly and accurately, and with less discomfort for the patient, the sub-gingival area surrounding a prepared tooth to be molded, for the formation of a dental prosthesis. It is yet another object of the present invention to provide means to pack thread into the sub-gingival area quickly and directly without requiring a separate cutting operation. A further object of the present invention is to provide mechanical means for packing a tooth with thread utilizing conventionally available reciprocating drive means, which can be manually powered or powered by compressed air or electricity, for example. It is a further object of the present invention to apply to the sub-gingival area a material which forms a solid in situ within the volume of the sulcus.

In accordance with the present invention, there is first provided mechanically driven means for pressing into place, in the sub-gingival area, conventional cord packing. This mechanically driven packing means comprises reciprocating drive means; a hammer means comprising an elongated shank member operatively and directly, but removably, connected to the reciprocating drive means, and a hammer member rigidly secured to the shank member so as to reciprocate therewith, the hammer member being secured to the shank end distal from the reciprocating drive means, the end surface of the hammer member being formed with a concave surface extending substantially transverse to the axis of the shank means; and external guide means rotatably secured to the reciprocating drive means at a first end thereof and extending along the length of and substantially coaxial with the hammer means, the external guide means substantially surrounding the hammer means along the length thereof and being provided with an opening at a second end distal from the driving means and surrounding the distal end surface of the hammer member, to permit reciprocal movement of the hammer surface from a first position inward of the guide second end to a second position substantially coterminous with the guide second end. The tip of the guide is so formed with rounded end edges as to be able to push aside the gum and other soft tissue adjacent the margin of the tooth. The guide means has at least one substantially planar external surface extending longitudinally along the guide from the open second end, and has a cross-section such that the width of the planar surface is greater than the width of the side external surfaces transverse to the planar surface.

In a second embodiment of the present invention, there is provided a syringe packing tool means designed to be secured to a syringe, or other pressurable reservoir, in place of the usual syringe needle point, the tool comprising a tool barrel portion having a first open end and a second end, reservoir, e.g., syringe fluid connection means in fluid flow connection between the reservoir and the second end of the tool barrel, the tool barrel being rotatably connected thereto. Preferably, the tool barrel portion extends transverse to the axis of the fluid connection means, e.g., the syringe barrel.

The tool barrel comprises a first external planar surface extending axially along the barrel portion from the open, first end inwardly towards the syringe connection, the open end of the barrel being shaped so as to permit insertion of the end of the barrel into the space between a tooth and its adjacent soft tissue, or gingiva, and having openings at the outer end facing transversely of the longitudinal axis of the barrel. Elastomeric material, which can form in situ, can be introduced through the tool barrel from the syringe, and into the space between a tooth and the soft tissue, or sulcus.

The mechanized dental packing tool of the present invention can be used with and powered by a conventional, commercially available reciprocating drive head, usually powered by electricity or a pressurized fluid, to which this device can be connected in a conventional manner. Such a drive head comprises conventional driving elements which do not, in themselves, form a part of the present invention and, thus, need not be illustrated in greater detail. Examples of suitable reciprocating drive means are shown for example in U.S. Pat. Nos. 3,552,022 to Axelsson and 4,629,426 to Levy. Conventionally available such dental driver handpieces are of a sufficiently slender, and elongated nature, often having a contra-angle head, to enable the dentist to easily and without injury to the patient, manipulate the device within the mouth and, most particularly, even with respect to the rearmost molars. Because of its conventional nature, the hand-held driver device need not be described in greater detail than is shown in the drawings, as such detail can be determined from the prior disclosures, e.g., as referred to above.

Alternatively, power for the hammer tool can be provided by manually operated means, such as a spring-loaded triggering mechanism or a foot-treadle operated device.

BRIEF DESCRIPTION OF THE DRAWINGS:

Preferred embodiments of this invention are described below, by way of example and not exclusion, by reference to the accompanying drawings which display portions of the present invention in schematic form. The details of such schematically shown portions will be readily known to those skilled in the art based upon the following verbal descriptions, and thus greater detail is not needed.

Referring to the drawings;

FIG. 3 is an exploded isometric view of the device of FIG. 1;

FIG. 4 is a cross-sectional elevation view of the hammer packing tool and driver handpiece in accordance with the present invention;

FIG. 5 is a partial section view taken along lines 5—5 of FIG. 4;

FIG. 6 is an enlarged detail view of the lower portion of FIG. 4;

FIG. 7 is a bottom plan view taken along lines 6—6 of FIG. 4;

FIG. 8 is an isometric view showing a second preferred embodiment of the present invention.

Referring to FIGS. 1 through 7, the mechanized packing hammer of the present invention comprises an outer guide barrel, generally indicated by the numeral 10, and including a barrel portion 11 having a substantially rectangular, but rounded out, cross-section wherein the wider sides 8 are substantially planar but the narrower sides 9 have a convex shape serving as a rounded point. The outer end of the barrel is open and the major sides 8 have rounded or chamfered ends 15.

Figure 1:
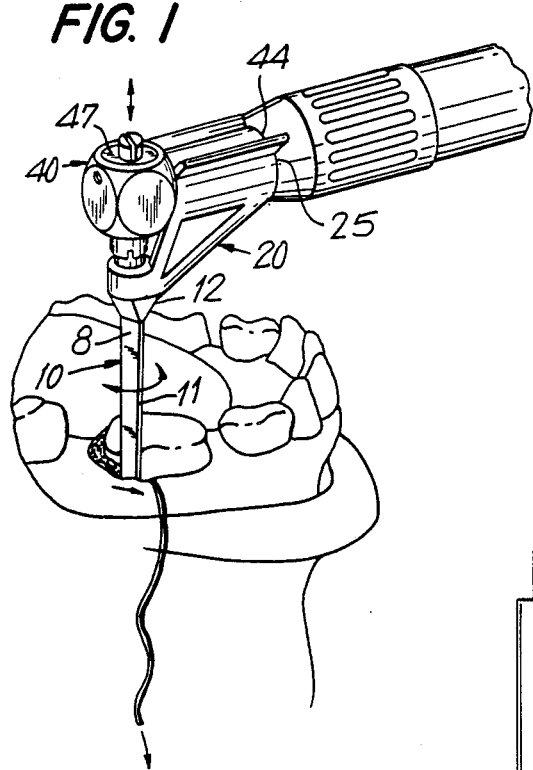
FIG. 1 is an isometric view of a reciprocating hammer tool, operating to pack a conventional packing thread around a prepared tooth between the tooth and the soft tissue, or gum.

An outwardly tapered or funnel-shaped transition portion 12 is secured to and integral with the second end of the barrel 11 and is pivotally connected to a support frame, generally indicated by the numeral 20. The wider end 13 or the transition portion is substantially circular in cross-section and includes a reentrant portion 18 which interlocks, or mates, with a similar circular reentrant portion 21 of the frame 20 to maintain the pivoting connection.

Extending coaxially within the guide member 10 is a reciprocable hammer tool, generally indicated by the numeral 30, which extends from within, or beyond, the distal end of the handpiece head, generally indicated by the numeral 40, to the open distal end 15 of the guide barrel 11. The hammer tool 30 comprises the cylindrical drive shank portion 31, a hammer shank portion 32 and the hammer head 33. The drive shank 31 has a slot formed at its driving end and the remaining material, i.e., forming two legs 31a, 31b, are flexibly elastic and can be pressed together to enable the shank to be pressed into the handpiece head 40; when the drive shank 31 is in place, and the two legs 31a, 31b spring apart to their normal position, the drive shank 31 cannot be pulled out of the handpiece head 40, in either axial direction until the two legs 31a, 31b are again pinched together. A circumferential welt 34 on the outer surface of the legs 31a, b, fits into a mating slot 42 in the handpiece head drive piston 44.

The hammer shank 32 extending towards the second end of the hammer piece 30 is substantially rectangular in cross-section, its sides being substantially parallel to the sides of the guide barrel 11. An intermediate transition portion 38 flares inwardly from the circumference of the drive shank 31 to the shape and size of the hammer shank 32, substantially coaxially with the transition portion 12 on the guide barrel.

The second end of the reciprocating hammer member 30 includes the hammer head 33. The hammer head 33 has a somewhat enlarged cross-section compared to the cross-section of the hammer shank 32, especially along the narrower dimension. In addition, the hammer end surface 133 includes a concavity defined by curved surface 37, to provide better control over any thread to be packed.

It is normal dental practice, after a tooth is prepared and as part of the procedure for applying a dental prosthesis, to prepare an impression of at least the portion of the mouth surrounding the prepared tooth. In making the impression, or mold, it is generally necessary to also include the gum, or soft tissue, surrounding the tooth, and to separate the soft tissue from the lower portion, or margin, of the tooth and to dry out that immediate portion of the soft tissue, i.e., the sulcus, which would otherwise be in contact with the lower tooth surface or margin. It is generally understood that the term "margin" refers to that portion of the lower part of the tooth, normally beneath the gum, but which must be in intimate contact with, the open end of the crown or cap.

In accordance with the method of use of the present invention, the procedure normally requires first pressing the open end 15 of the guide barrel 10 against the gum line of the tooth, so as to separate the gum, or soft tissue, from the tooth surface. A packing thread (T, in FIG. 6) is placed in that location and the handpiece turned on such that the hammer head surface 133 pushes the thread down into the sulcus, or space between the gum and the tooth surface.

Figure 2:
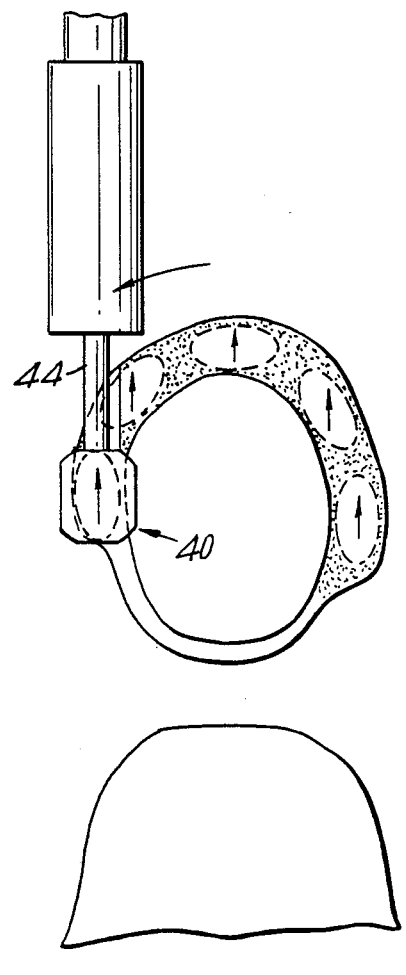
FIG. 2 is a top plan schematic view showing the partially packed tooth of FIG. 1.

The shape of the guide barrel 10, specifically its narrow rounded ends and flat sides, permits the operator to push the guide piece around the tooth, keeping one wide flat surface 11 against the gum surface to separate the gum tissue from the tooth surface as the hammer head 33 presses additional packing thread, which is simultaneously being fed in between the tooth and the gum. The axis of the hammer shank 32 is maintained substantially parallel to the axis of the tooth, and the flat wide sides 11 of the guide 10 are maintained in contact with the gum, and the tooth surface when the gum is close to the tooth. This is shown, more clearly in FIGS. 1 and 2; in FIG. 2, a partially packed tooth is shown, and the changing orientation of the swivelling guide member 10 as the operator moves the tool around the tooth surface packing the thread into place, is shown by phantom lines. As the guide member 11 is moved around the tooth, the pressure of the planar guide surface 8 against the gum surface causes the guide member 11 to swivel and thus to maintain the desired alignment.

In the simplest case shown in FIGS. 1 through 7, the hammer shank 32 swivels together with the guide barrel 11, as the shape of the hammer shank is similar to that of the rectangular guide barrel. However, if desired, as shown in FIG. 8, a manual wheel 51 can be secured into the slot between the drive shank legs 31a,b, and used to turn the hammer piece 30 manually to a desired orientation, either during the packing operation or initially.

As shown in the drawings, a portion of a commonly available reciprocating handpiece is shown having a drive barrel portion 44, which is gripped by an elastic spring-loaded clip 25, forming a part of the frame 20 of the packing tool. The clip 25 is spring-loaded so as to tightly grip the barrel 44, thus securing the device in place. A secondary support member 26 is provided resting against the front end of the handpiece head 40 to further stabilize the guide during use.

To provide some general background, the conventional reciprocating drive handpiece shown provides means to convert the rotary motion of a shaft 43, having an eccentrically arranged drive tip 48, into reciprocating motion, by virtue of the action of the tip 48 against the sleeve piston 45: The eccentric tip 48 moves, back and forth between the enlarged top and bottom flanges 46, 47, thus pushing the sleeve 45 and thus the hammer 30 in an axially reciprocating motion.

It has been found preferable to provide a concavity in the hammer head surface 33, having a radius of curvature at least twice that of the radius of the packing cord. The total width of the hammer head, in the dimension encompassing the curved portion is preferably no greater than 1.4 mm, i.e., the narrower dimension. The wider dimension of the guide member is preferably about 2.4 mm, and the narrow dimension about 1.2 mm; the interior barrel chamber within the guide barrel 11 is preferably similar in cross-section to the cross-section of the hammer member, but sufficiently larger not to obstruct the axial movement of the hammer. Most preferably, the narrower cross-section dimension of the guide is not larger than the major cross-section dimension of the hammer, so that pivoting either member causes the other member to follow. Preferably, at least the guide tip portion 15 is somewhat thickened along one of the major surfaces 8, which should be the side facing the tooth surface. This maintains a suitable distance to prevent the hammer from striking the tooth.

The packing thread is usually impregnated with a drying agent to aid in drying the soft tissue surrounding the prepared tooth. The packing thread is removed prior to placing the impression material around the tooth, to prepare the mold impression. A supply of packing thread, as on a spool, or roller, can be rotatably secured about its axis to the tool frame 20, or to another portion of the handpiece, if desired.

In accordance with a further aspect of the present invention, the mold material, for obtaining an accurate impression of the tooth margin, can be applied using a special tapered syringe barrel, in accordance with this invention, after the packing is removed, but before the gum has a chance to retract and remoisten itself.

In accordance with the second aspect of this invention, a conventional syringe is modified by the substitution for the usual needle tip, of a curable elastomeric material dispensing tool, generally indicated by the numeral 100, having a tip designed to pack in a ribbon shape the curable resinous material between the soft surrounding gum and the margin of the tooth.

The ribbon forming packing tool of the present invention comprises a tool barrel, generally indicated by the numeral 110, opening outwardly at one end 108 and integrally connected at its second end to an outwardly tapered or funnel-shaped transition portion 116, which has a substantially circular second end cross-section 117. The second end 117 of the transition portion is pivotally and sealably connected to the tool head 118, which is in turn transversely connected, preferably perpendicularly, to a feed tube 119, designed to be connected to the outlet from a syringe barrel 130.

The tool barrel 110 preferably has a substantially constant oval or rounded rectangular cross-section along most of its length; and has two opposed major surfaces 109, 111, at least one of such major surfaces 109, 111 preferably is substantially planar along its entire length between the junction with the connecting portion 116 and the outer tip, generally indicated by the numeral 108. The two opposing narrower sides of the tool barrel 110 have a preferably rounded, convex shape to provide a relatively mild point curve 114, or prow, to aid in pushing aside soft tissue, as the barrel is moved around the tooth.

At the outer tip 108 of the barrel, the opposing narrower sides 114 of the tool barrel are partially cut away to form the pointed tips 124, 128: The tip 124 at the end of the flat major surface 111 is cut away to a relatively narrow point 124, defined by curved surface 127, and curves radially inwardly towards the second major surface 109. The tip 128 of the second major surface 109 comes to a more rounded end defined by curved surface 125, and is generally broader and more spade-like in appearance as compared to the shorter end 124. In addition, the more spade-like tip 128 extends beyond the end of the shorter point 124 and curves inwardly so as to extend beyond and around the shorter point 124. These inwardly curving tips 124, 128 surround sideward facing openings, which are defined by the curved edge surfaces 125, 127, for expelling the resin in a ribbon-like form.

The entire resin packing tool 100, is secured to the syringe barrel 130 at the usual syringe tip connection 131 via feed tube 119. The feed tube 119 extends into the side of the tool barrel head 118 preferably substantially perpendicularly to the axis of the tool barrel 110. The swivel connection 117 between the funnel portion 116 and the tool barrel head 118 is designed to be substantially fluid tight to prevent loss of any material transmitted from the syringe through the tool, and is similar in construction to that shown for the hammer guide in FIG. 4, above.

In the preferred embodiment shown in the drawings, there is also provided a pistol-type grip for the syringe barrel. The simple grip shown in FIG. 9, generally indicated by numeral 160, forms a slidable snug fit around the syringe barrel 130. The rearward grip portion 162 is braced against the hilt 163 of the syringe, and the forward grip portion 154 is spring loaded against the outer surface of the syringe barrel 130.

Figure 10:
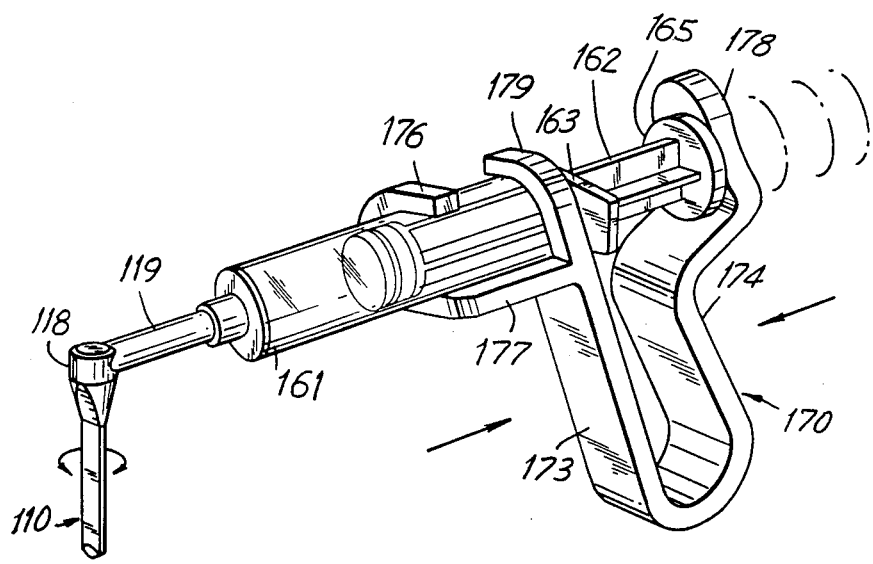
FIG. 10 is an isometric view of a second embodiment of a resin packing syringe tool of the present invention.
Figure 11:
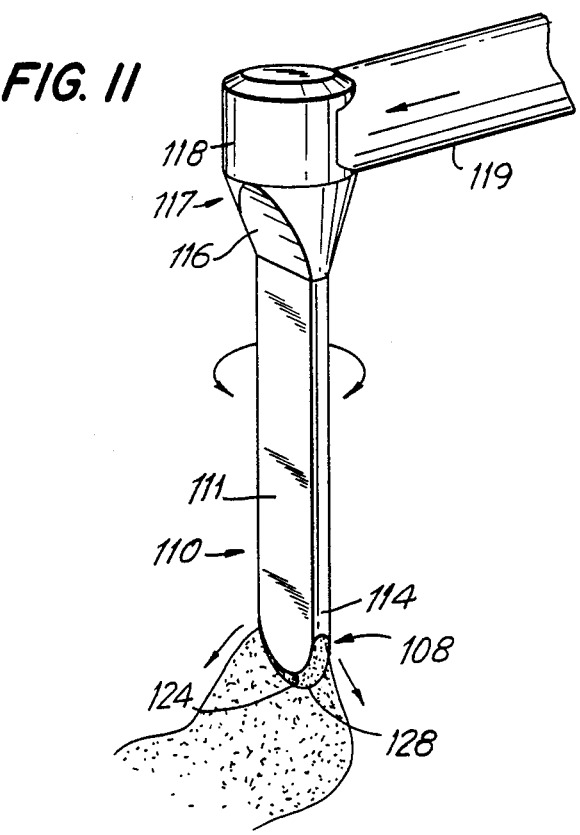
FIG. 11 is an enlarged partial isometric view of the operating end of the device of FIG. 9 showing a resinous paste being extruded.
Figure 12:
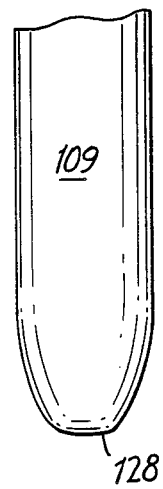
FIG. 12 is an enlarged rear elevation view of the tip of the device of FIG. 11.
Figure 13:
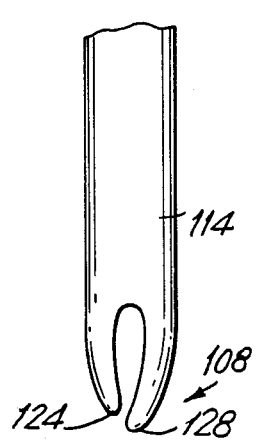
FIG. 13 is an enlarged side elevation view of the device of FIG. 11.
Figure 14:
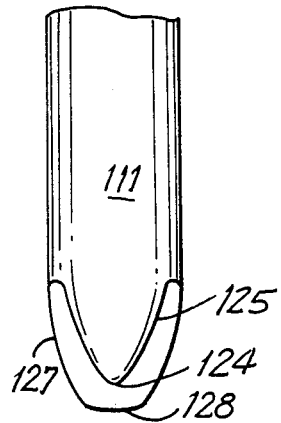
FIG. 14 is an enlarged front elevation view of the tip of the device of FIG. 11.
Figure 15:
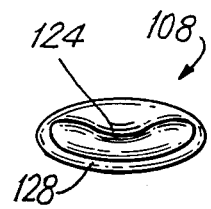
FIG. 15 is a bottom view of the device of FIG. 11.

The more preferred embodiment of FIG. 10 includes clamping means 176, 179 for gripping the syringe barrel 130, which rests upon the grip platform portion 177. The clamping means 176, 177, 179 are integral with the grip handle, generally indicated by the numeral 170, and which includes a forward handle portion 173, in immediate connection with the clamping means finger 179 and the clamping platform 177. The clamping finger 179 is braced against the syringe hilt 163. The rear handle portion 174 is integral with and in immediate connection with the pressure hammer 178, which is pressed against the syringe plunger head 165.

The syringe plunger 162 and barrel 130 are of substantially conventional manufacture as shown in the drawings.

Figure 16:
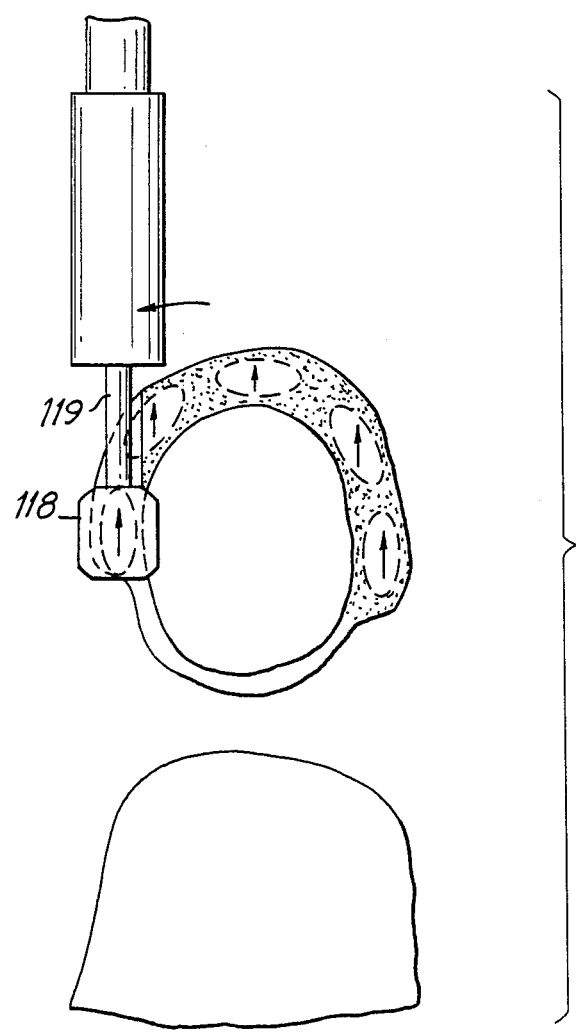
FIG. 16 is a top plan schematic view showing the formation of the elastomeric impression material.

In accordance with conventional dental practice, after a tooth is prepared to accept a crown or cap, and the surrounding soft tissue has been freed and deflected from the tooth margin surface, and the sulcus dried, using the packing thread as described above, for example, the packing thread is removed and the syringe tool tip 108 is inserted into the sulcus space between the soft tissue and the tooth surface, as shown for example in FIG. 16. The relatively flat tool barrel surface 111 is pressed against the tooth surface and the rounded major surface 109 is pressed, at its lower spade end 128, against the soft tissue, forcing it away from the tooth surface.

The syringe can be filled with a self-curing elastomeric precursor material of a type conventionally used for the formation of dental impressions. Such curable material is generally a resinous precursor of an elastomeric polymer, which is safely curable in situ in the mouth of a patient. The syringe plunger 162 is depressed while moving the tool barrel tip 110 around the tooth margin. The planar tool barrel surface 111 is maintained pressed against the outer surface of the tooth to maintain the tool barrel 110 in the desired orientation. As the tool barrel 110 is moved around the tooth, the barrel 110 can swivel, thereby permitting the continuous circumferential movement around the tooth, without lifting up the tool, thus providing for a continuous and smooth application of the molding resin. As the tool barrel 110 is pushed around the tooth surface, the relatively pointed side surfaces 114 act to push away the soft tissue from the tooth to make way for the resin.

Figure 9:
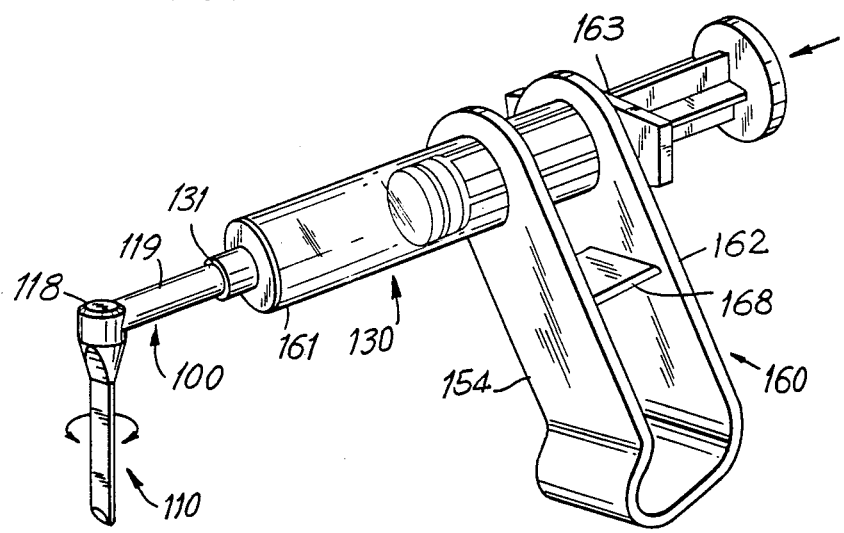
FIG. 9 is an isometric view of a resin packing syringe tool of the present invention.

The pistol grip 160 or 170 provides for comfortable and accurate movement of the tool around the tooth. The simpler grip 160 of FIG. 9 is held by one hand while the thumb of that hand presses against the syringe plunger head 165. The cross piece 168 prevents the two halves 154, 161 of the handle grip 160 from being squeezed together when holding the grip. When utilizing the grip of FIG. 10, squeezing the handle portions 174, 173 together, results in the depression of the syringe plunger 162, as the handle hammer portion 147 is pressed against the plunger head 165. In both embodiments, the other hand is free to guide, or to provide extra support, for the tool barrel 110.

The Patentable Embodiments of this Invention Which are Claimed are as follows:

1. For use in a dental device comprising reciprocating drive means, the reciprocating drive means comprising a reciprocating member for providing reciprocating motion and designed to retain a dental tool, the dental tool comprising:

frame means for securing the dental tool to the reciprocating drive means; a hammer member designed to be retained by said reciprocating member, and comprising a drive shank portion, a hammer shank portion formed integral with and extending axially from one end of the drive shank portion and a hammer head secured to the distal end of the hammer shank, and having a hammer end surface; and a hammer barrel, forming a sheath for the hammer member and coaxial therewith, the hammer barrel being rotatably secured to the frame means and being open at an end substantially surrounding the hammer head, the hammer head having a length relative to the hammer barrel such that at one extreme of its reciprocating movement, the end of the hammer is substantially coextensive with the end of the hammer barrel, and at the other extreme of its reciprocating movement, is further within the barrel, the hammer being designed to pack dental thread around the margin of a prepared tooth preparatory to making a dental impression, when the hammer is driven by the reciprocating member.

2. The dental tool of claim 1 wherein the hammer barrel and hammer shank and hammer head have an elongated rounded transverse cross-section having opposing narrow sides and opposing wider sides and wherein the narrow sides of the hammer barrel are rounded in a convex external direction so as to form a suitable prow for pushing away soft tissue surrounding the gum as the thread is packed into place.

3. The dental tool of claim 1 wherein at least one of the wider sides of the hammer barrel is substantially planar at the portion adjacent the open end of the hammer barrel.

4. The dental tool of claim 1 wherein the hammer end surface portion is concave.

5. The dental tool of claim 1 wherein the hammer can be manually rotated, the hammer and the hammer barrel being so juxtaposed that the rotation of either of the hammer and hammer barrel results in rotation of the other of the hammer and hammer barrel.

* * * * *